(12) United States Patent
Kamimura et al.

(10) Patent No.: US 9,211,053 B2
(45) Date of Patent: Dec. 15, 2015

(54) MEDICAL APPARATUS, DISPOSABLE MEDICAL DEVICE, AND MEDICAL SYSTEM

(71) Applicant: OLYMPUS CORPORATION, Tokyo (JP)

(72) Inventors: Kenji Kamimura, Hachioji (JP);
Yoshimine Kobayashi, Hachioji (JP);
Seiki Toriyama, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/947,407

(22) Filed: Jul. 22, 2013

(65) Prior Publication Data

US 2014/0031629 A1   Jan. 30, 2014

Related U.S. Application Data

(60) Provisional application No. 61/675,157, filed on Jul. 24, 2012.

(51) Int. Cl.
*A61B 1/06*  (2006.01)
*A61B 1/00*  (2006.01)
*A61B 1/07*  (2006.01)
*A61B 1/018* (2006.01)

(52) U.S. Cl.
CPC ......... *A61B 1/00103* (2013.01); *A61B 1/00062* (2013.01); *A61B 1/018* (2013.01); *A61B 1/0669* (2013.01); *A61B 1/07* (2013.01)

(58) Field of Classification Search
CPC ... A61B 1/00103; A61B 1/00062; A61B 1/07
USPC .............................. 606/15, 16; 600/181, 182
See application file for complete search history.

(56) References Cited

U.S. PATENT DOCUMENTS

| | | | |
|---|---|---|---|
| 6,385,162 B1 * | 5/2002 | Nagase et al. | 369/288 |
| 6,847,490 B1 * | 1/2005 | Nordstrom et al. | 359/642 |
| 2004/0260276 A1 * | 12/2004 | Rudko et al. | 606/15 |
| 2005/0086679 A1 * | 4/2005 | Murakami et al. | 720/718 |
| 2005/0113815 A1 * | 5/2005 | Ritchie et al. | 606/15 |

FOREIGN PATENT DOCUMENTS

JP   A-2003-501124   1/2003
WO   WO 00/74556 A2  12/2000

* cited by examiner

*Primary Examiner* — Anhtuan T Nguyen
*Assistant Examiner* — Alexandra Newton
(74) *Attorney, Agent, or Firm* — Oliff PLC

(57) ABSTRACT

A medical apparatus is detachably connected with a disposable medical device to be inserted into a subject, and performs a specified treatment. The medical apparatus includes an alteration unit that performs an alteration process of altering the medical device, and a control unit that causes the alteration unit to perform the alteration process at the end of the treatment by the medical apparatus.

6 Claims, 9 Drawing Sheets

MEDICAL APPARATUS, DISPOSABLE MEDICAL DEVICE, AND MEDICAL SYSTEM

CROSS-REFERENCE TO RELATED APPLICATIONS

This application is based upon and claims the benefit of priority from U.S. Provisional Patent Application No. 61/675,157, filed on Jul. 24, 2012, the entire contents of which are incorporated herein by reference.

BACKGROUND OF THE INVENTION

1. Field of the Invention

The disclosure relates to a medical apparatus that treats a subject, a disposable medical device that may be attached to and detached from the medical apparatus, and a medical system that includes the medical apparatus and the disposable medical device.

2. Description of the Related Art

Recently, in medical service field, to prevent a pathogen infection between subjects during an examination or a treatment of a subject, a medical device such as a disposable measurement probe and an electrosurgical knife is frequently used. A disposable medical device may hardly have a difference in appearance between before and after use. This type of disposable medical device may be reused. For this reason, there is a known technology for preventing a disposable medical device from being reused by radiating an ultraviolet ray to the medical device during an examination of a body tissue, thereby altering the medical device (see Japanese National Publication of International Patent Application No. 2003-501124).

SUMMARY OF THE INVENTION

In accordance with some embodiments, a medical apparatus, a disposable medical device, and a medical system are presented.

In some embodiments, a medical apparatus is detachably connected with a disposable medical device to be inserted into a subject, performs a specified treatment, and includes: an alteration unit that performs an alteration process of altering the medical device; and a control unit that causes the alteration unit to perform the alteration process at the end of the treatment by the medical apparatus.

In some embodiments, a disposable medical device, which is to be detachably connected to a medical apparatus that performs a specified treatment, includes: a proximal end portion that is connected to the medical apparatus; and a mark generator that is provided in the proximal end portion, and generates a mark indicating completion of use by an action of at least one of light, heat, and electricity.

In some embodiments, a medical system includes a medical apparatus that performs a specified treatment, and a disposable medical device to be detachably connected to the medical apparatus and to be inserted into a subject. The medical apparatus includes an alteration unit that performs an alteration process of altering the medical device, and a control unit that causes the alteration unit to perform the alteration process at the end of the treatment by the medical apparatus.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
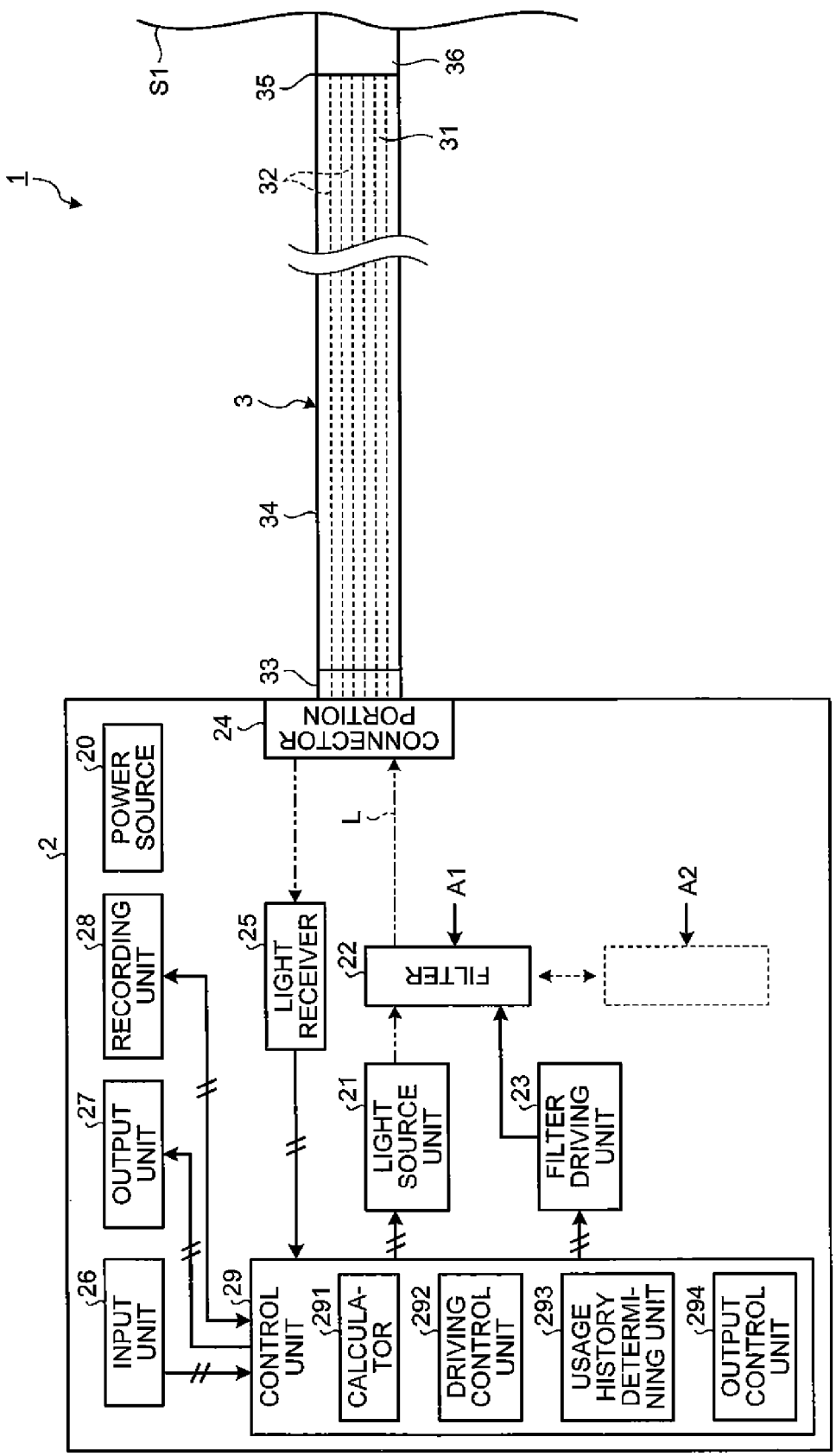
FIG. 1 is a block diagram schematically illustrating a configuration of a bio-optical measurement system according to a first embodiment of the present invention.

Hereinafter, as preferred embodiments (hereinafter, referred to as "embodiments") of a medical apparatus, a disposable medical device, and a medical system according to the invention, a bio-optical measurement device using an LEBS (Low-Coherence Enhanced Backscattering Spectroscopy) technology, and a disposable measurement probe using the bio-optical measurement device will be described by way of example with reference to the drawings. In addition, in the description of the drawings, the same portion will be denoted by the same reference numeral. It should be noted that the present invention is not limited to the embodiments.

First Embodiment

FIG. 1 is a block diagram schematically illustrating a configuration of a bio-optical measurement system according to a first embodiment of the present invention.

A bio-optical measurement system 1 illustrated in FIG. 1 includes a bio-optical measurement device 2, as a medical apparatus, which detects the property (characteristic) of an object S1 to be measured that is a scatterer by performing an optical measurement on the object S1 to be measured, and a measurement probe 3, as a disposable medical device inserted into a subject, which may be attached to and detached from the bio-optical measurement device 2. Herein, the object S1 to be measured is a body tissue, a blood flow, an organ such as a stomach or a pancreas, a mucosa, and the like.

First, the bio-optical measurement device 2 will be described. The bio-optical measurement device 2 includes a power source 20, a light source unit 21, a filter 22, a filter driving unit 23, a connector portion 24, a light receiver 25, an input unit 26, and an output unit 27, a recording unit 28, and a control unit 29. The power source 20 supplies power to each unit of the bio-optical measurement device 2.

The light source unit 21 radiates an illumination light including as a component (10 to 400 nm) of light in a specified wavelength band, for example, light in a wavelength band of an ultraviolet ray to the measurement probe 3 described below through the connector portion 24. The light source unit 21 is implemented using an incoherent optical source such as a white light emitting diode (LED), a xenon lamp, a tungsten lamp, and a halogen lamp, and a plurality of lenses. Examples of the lenses may include a condenser lens and a collimate lens.

The filter 22 is provided on a first position A1 passing through a light path L of an illumination light radiated by the light source unit 21, and only transmits a specified wavelength band included in the illumination light. Specifically, the filter 22 is implemented using an ultraviolet cut filter to block light in a wavelength band of an ultraviolet ray included in the illumination light, and transmit light in other wavelength bands. In addition, the filter 22 is provided to be able to advance and retreat between the first position A1 and a second position A2 away from the light path L within the bio-optical measurement device 2.

The filter driving unit 23 is constructed using a stepping motor, a DC motor, and the like, and moves the filter 22 between the first position A1 and the second position A2 under control of the control unit 29. In the first embodiment, the light source unit 21, the filter 22, and the filter driving unit 23 function as an alteration unit.

The measurement probe 3 is detachably connected to the connector portion 24. The connector portion 24 propagates an illumination light passing through the filter 22 to the measurement probe 3, and propagates light entering from the measurement probe 3 to the light receiver 25.

The light receiver 25 receives and measures an optical feedback of an illumination light that is radiated from the measurement probe 3 and is reflected and/or scattered on an object Si to be measured. The light receiver 25 is implemented using a plurality of spectrometers or light receiving sensors, and the like. Specifically, the light receiver 25 is provided with spectrometers the number of which corresponds to the number of light receiving fibers of the measurement probe 3 to be described below. The light receiver 25 measures a spectral component and an intensity distribution of a scattering light entering from the measurement probe 3, and outputs the measurement result to the control unit 29.

The input unit 26 receives an indication signal that indicates an activation of the bio-optical measurement device 2, an indication signal that terminates a measurement of the object S1 to be measured performed by the bio-optical measurement device 2, or an indication signal that indicates other various operations, and outputs the indication signal to the control unit 29. The input unit 26 is implemented using a push-type switch, a touch panel, and the like.

The output unit 27 outputs, under control of the control unit 29, various types of information in the bio-optical measurement device 2, for example, information indicating completion of use of the measurement probe 3 connected to the connector portion 24. The output unit 27 is implemented using a display such as a liquid crystal display or an organic electro luminescence (EL) display, a speaker, and the like.

The recording unit 28 records various programs for operating the bio-optical measurement device 2, and various data and various parameters used for optical measurement processing. The recording unit 28 temporarily records information during processing of the bio-optical measurement device 2. In addition, the recording unit 28 records a measurement result of the object S1 to be measured from the bio-optical measurement device 2. The recording unit 28 is implemented using a volatile memory or a non-volatile memory. The recording unit 28 may be constructed using a memory card and the like mounted from an outside of the bio-optical measurement device 2.

The control unit 29 performs an overall control on the bio-optical measurement device 2 by transmitting instruction information or data corresponding to each unit of the bio-optical measurement device 2. The control unit 29 is constructed using a central processing unit (CPU) and the like. The control unit 29 includes a calculator 291, a driving control unit 292, a usage history determining unit 293, and an output control unit 294.

The calculator 291 performs a plurality of calculation processes based on a measurement result from the light receiver 25, and calculates a characteristic value related to the property of the object S1 to be measured. A type of characteristic value is set, for example, according to an instruction signal received by the input unit 26.

When an instruction signal that terminates a measurement of the object S1 to be measured is received from the input unit 26, the driving control unit 292 drives the filter driving unit 23 to move the filter 22 from the first position A1 to the second position A2 as an altering process of altering the disposable measurement probe 3.

When performing a calibration process on the measurement probe 3, the usage history determining unit 293 determines a usage history of the measurement probe 3 based on a measurement result from the light receiver 25. Specifically, the usage history determining unit 293 determines whether the measurement result from the light receiver 25 is greater than or equal to a specified threshold value due to an alteration of the property of the measurement probe 3. The usage history determining unit 293 determines that the measurement probe 3 has not been used when the measurement result is greater than or equal to the threshold value, and determines completion of use of the measurement probe 3 when the measurement result is not greater than or equal to the threshold value.

When the usage history determining unit 293 determines that the measurement probe 3 is in use, the output control unit 294 causes the output unit 27 to output information indicating completion of use of the measurement probe 3.

Next, the measurement probe 3 will be described. The measurement probe 3 includes a plurality of light fibers made of a material, an optical property of which alters (deteriorates) due to a transmission of light in a specified wavelength band, for example, an ultraviolet ray. Specifically, the measurement probe 3 is implemented using an illumination fiber 31 that radiates an illumination light to the object S1 to be measured, and a plurality of light receiving fibers 32 where an optical feedback of an illumination light reflected and/or scattered on the object S1 to be measured enters at different angles. The illumination fiber 31 and the light receiving fibers 32 are arranged such that distal end portions are parallel to each other. In addition, the measurement probe 3 includes a proximal end portion 33, a flexible portion 34, a distal end portion 35, and a rod lens 36.

The proximal end portion 33 is detachably connected to the connector portion 24. The flexible portion 34 has flexibility, propagates an illumination light radiated from the bio-optical measurement device 2 to the distal end portion 35 including a distal end where an edge face of the illumination fiber 31 is exposed, and propagates an optical feed back of an illumination light entering through the distal end portion 35 to the bio-optical measurement device 2. The distal end portion 35 radiates an illumination light propagated from the flexible portion 34 through the rod lens 36 to the object S1 to be measured, and an optical feedback of an illumination light reflected and/or scattered on the object S1 to be measured enters through the rod lens 36. In addition, the distal end portion 35 is provided with the rod lens 36 having permeability as an optical member. The rod lens 36 forms a cylindrical shape so that a distance between the object S1 to be measured and a distal end of the illumination fiber 31 and the light receiving fiber 32 is constant. In addition, a UV coating process for blocking an ultraviolet ray is performed on the rod lens 36 and/or a boundary surface between the rod lens 36 and the distal end portion 35. Further, the rod lens 36 is formed using a member, an optical property of which is altered by a radiated ultraviolet ray, for example, photochromic glass. Referring to FIG. 1, an example of the measurement probe 3 including two light receiving fibers 32 is described. However, three or more light receiving fibers 32 may be used. Furthermore, the number of the illumination fibers 31 may be appropriately changed according to the object S1 to be measured.

Figure 2:
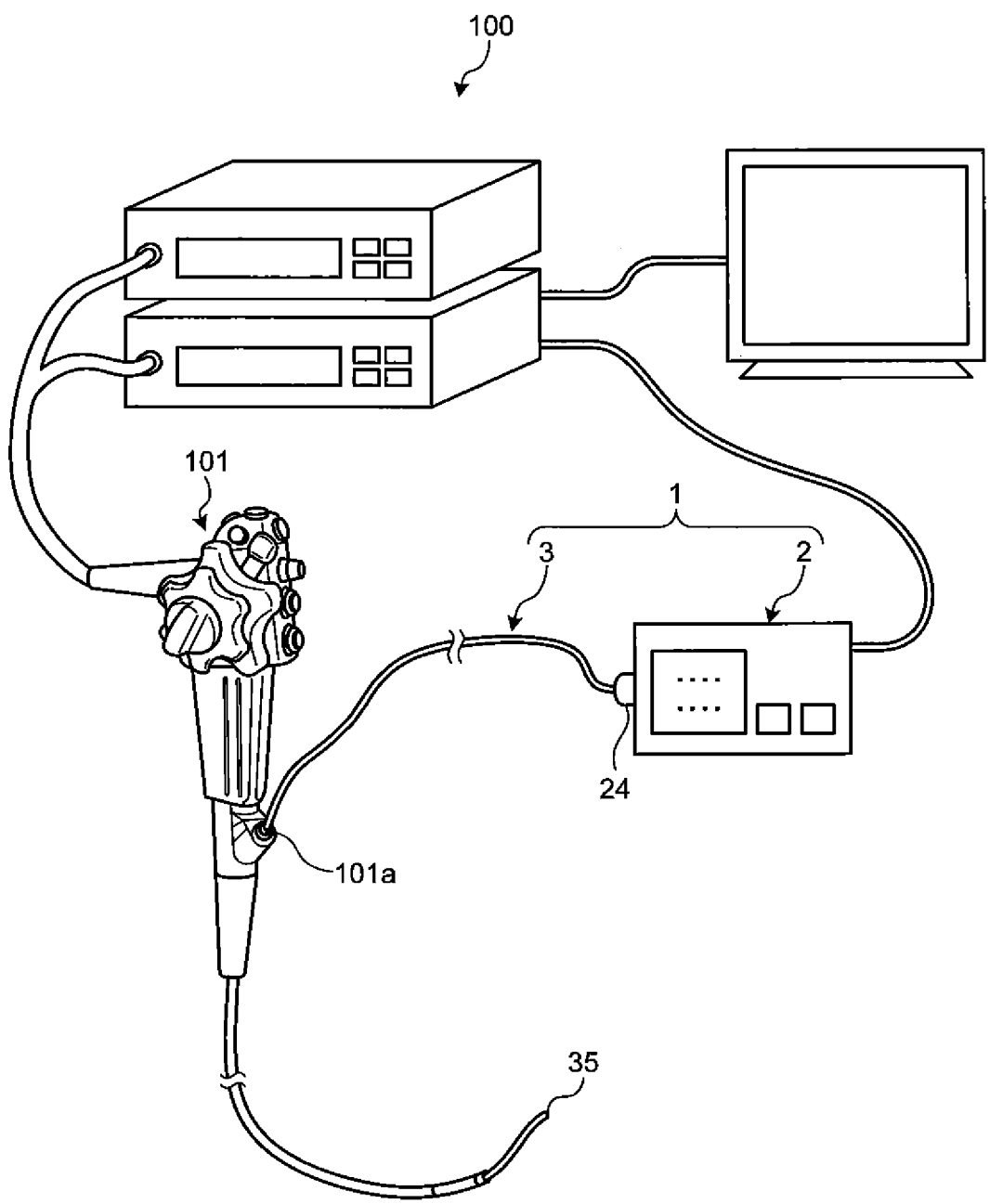
FIG. 2 is a diagram illustrating a circumstance in which the bio-optical measurement system according to the first embodiment of the present invention is used in an endoscopic system.

As illustrated in FIG. 2, in the bio-optical measurement system 1 constructed as described in the foregoing, the measurement probe 3 is inserted into a subject through a treatment tool channel 101a provided in an endoscopic device 101 (endoscope) of an endoscopic system 100, the illumination fiber 31 radiates an illumination light to the object S1 to be measured, and the light receiving fibers 32 receive an optical feedback of the illumination light reflected and/or scattered on the object S1 to be measured at different angles, and propagate and radiate the optical feedback to the light receiver 25 of the bio-optical measurement device 2. Thereafter, the calculator 291 calculates a characteristic value of the property of the object S1 to be measured based on a measurement result of the light receiver 25.

Figure 3:
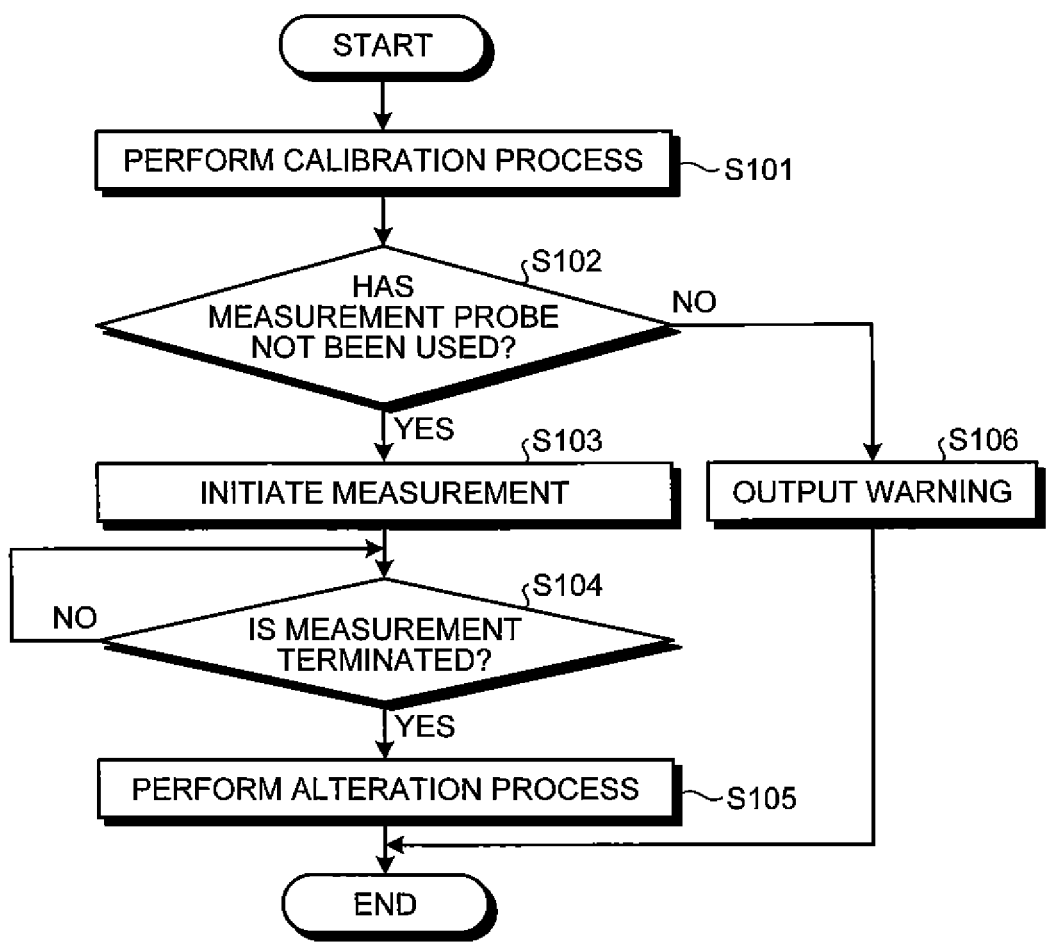
FIG. 3 is a flowchart illustrating processes performed by the bio-optical measurement system according to the first embodiment of the present invention.

Next, processes performed by the bio-optical measurement system 1 will be described. FIG. 3 is a flowchart illustrating an outline of processes performed by the bio-optical measurement system 1.

As illustrated in FIG. 3, when the measurement probe 3 in which a calibration member such as a white plate is attached to the rod lens 36 is connected to the connector portion 24 of the bio-optical measurement device 2, the control unit 29 performs a calibration process (step S101). Specifically, the control unit 29 radiates an illumination light to the light source unit 21, and performs a calibration process of the measurement probe 3 and the bio-optical measurement device 2 based on a measurement value of receiving an optical feedback of an illumination light reflected on the white plate by the light receiver 25.

Subsequently, the usage history determining unit 293 determines whether the measurement probe 3 has not been used (step S102). Specifically, the usage history determining unit 293 determines whether a calculation result calculated by the calculator 291 is greater than or equal to a specified threshold value. The usage history determining unit 293 determines that the measurement probe 3 has not been used when the calculation result is greater than or equal to the threshold value, and determines that the measurement probe 3 has been used when the calculation result is not greater than or equal to the threshold value. When the usage history determining unit 293 determines that the measurement probe 3 has not been used (Yes in step S102), the bio-optical measurement system 1 proceeds to step S103.

Subsequently, the control unit 29 causes the light source unit 21 to radiate an illumination light to the measurement probe 3 to initiate a measurement of the object S1 to be measured (step S103).

Thereafter, the control unit 29 determines whether an instruction signal that terminates the measurement of the object S1 to be measured is received from the input unit 26 (step S104). When the control unit 29 determines that the instruction signal that terminates the measurement of the object S1 to be measured is received (Yes in step S104), the bio-optical measurement system 1 proceeds to step S105. On the contrary, when the control unit 29 determines that the instruction signal that terminates the measurement of the object S1 to be measured is not received (No in step S104), the bio-optical measurement system 1 continues with the determination of step S104.

Subsequently, the driving control unit 292 performs an altering process of driving the filter driving unit 23, moving the filter 22 from the first position A1 to the second position A2, and then radiating an illumination light to the light source unit 21 to alter the measurement probe 3 (step S105). In this way, the property of the illumination fiber 31 and the rod lens 36 of the measurement probe 3 alters due to an ultraviolet ray, and thus the measurement probe 3 deteriorates. On this occasion, since a UV coating process is performed on the rod lens 36, the ultraviolet ray may not pass through the rod lens 36, and is not radiated to the outside of the measurement probe 3. Thereafter, the bio-optical measurement system 1 terminates this process.

In step S102, when the usage history determining unit 293 determines that the measurement probe 3 has been used (No in step S102), the output control unit 294 causes the output unit 27 to output a warning indicating that the measurement probe 3 has been used (step S106). Thereafter, the bio-optical measurement system 1 terminates this process.

According to the above-described first embodiment, when an instruction signal that terminates a measurement of the object S1 to be measured is input from the input unit 26, the control unit 29 drives the filter driving unit 23 to move the filter 22 from the first position A1 to the second position A2, thereby altering an optical property of the measurement probe 3. In this way, without degrading accuracy of an examination result, it is possible to reliably prevent the disposable measurement probe 3 from being reused.

Further, according to the first embodiment, the usage history determining unit 293 determines whether the measurement probe 3 has not been used based on a value of an optical feedback of an illumination light received by the light receiver 25. When the usage history determining unit 293 determines that the measurement probe 3 has been used, the output control unit 294 causes the output unit 27 to output information indicating that the measurement probe 3 has been used. Accordingly, a user may recognize the used measurement probe 3 during a calibration of the bio-optical measurement device 2.

In addition, according to the first embodiment, since a UV coating process is performed on the rod lens 36 and a boundary surface of the distal end portion 35 of the measurement probe 3 and the rod lens 36, it is possible to reliably prevent an ultraviolet ray from being radiated to the outside of the measurement probe 3.

In the first embodiment, when the usage history determining unit 293 determines that the measurement probe 3 has been used, the control unit 29 may forbid a measurement of the property of the object S1 to be measured. In this way, it is possible to prevent the disposable measurement probe 3 from being reused.

In addition, in the first embodiment, when the usage history determining unit 293 determines that the measurement probe 3 has been used, the control unit 29 may stop driving the bio-optical measurement device 3 by controlling the power source 20. In this way, it is possible to reliably prevent the disposable measurement probe 3 from being reused.

Second Embodiment

Next, a second embodiment of the invention will be described. A bio-optical measurement system according to the second embodiment further includes an alteration light source unit that alters a measurement probe. For this reason, when description is made, the same element as that of the bio-optical measurement system according to the above-described first embodiment will be denoted by the same reference numeral.

Figure 4:
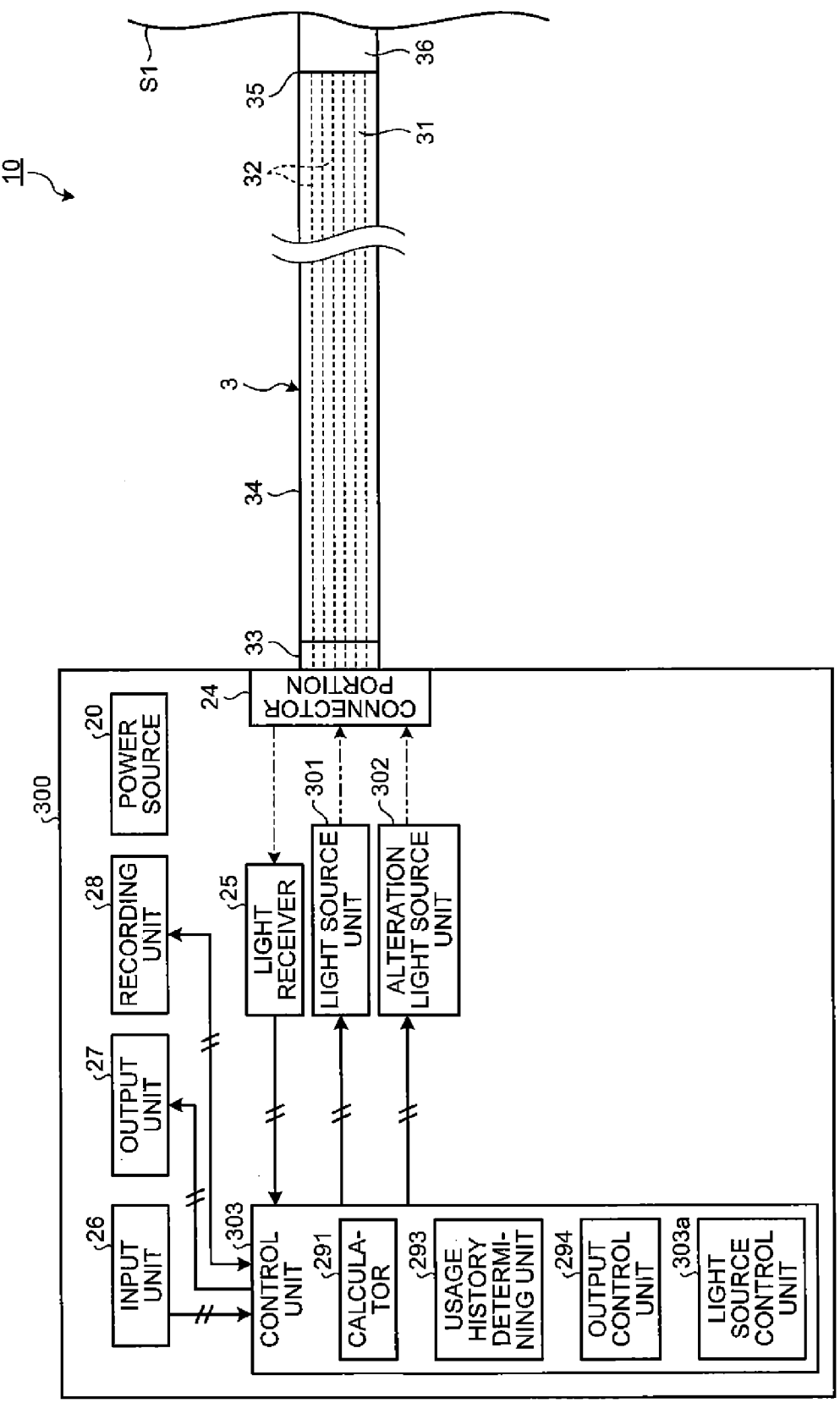
FIG. 4 is a block diagram schematically illustrating a configuration of a bio-optical measurement system according to a second embodiment of the present invention.

FIG. 4 is a block diagram illustrating a configuration of a bio-optical measurement system according to the second embodiment of the present invention.

A bio-optical measurement system 10 illustrated in FIG. 4 includes a measurement probe 3, and a bio-optical measurement device 300 that detects the property of an object S1 to be measured by performing an optical measurement on the object S1 to be measured.

The bio-optical measurement device 300 includes a power source 20, a connector portion 24, a light receiver 25, an input unit 26, and output unit 27, a recording unit 28, a light source unit 301, an alteration light source unit 302, and a control unit 303.

The light source unit 301 radiates an illumination light to an illumination fiber 31 of the measurement probe 3 through the connector portion 24. The light source unit 301 is implemented using an incoherent optical source such as a white LED, a xenon lamp, a tungsten lamp, and a halogen lamp, an optical system such as a condenser lens and a collimate lens, an ultraviolet cut filter that blocks light in a wavelength band of an ultraviolet ray and the like included in an illumination light radiated by a light source, and the like.

The alteration light source unit 302 radiates an alteration light that alters the measurement probe 3 to the measurement probe 3 through the connector portion 24. Herein, the alteration light corresponds to light including light in a wavelength band of an ultraviolet ray. The alteration light source unit 302 is implemented using an optical source such as a xenon lamp, a tungsten lamp, and a halogen lamp, and an optical system such as a condenser lens and a collimate lens. In addition, the alteration light source unit 302 is provided within the bio-optical measurement device 300 so that the alteration light is not total reflected within the measurement probe 3. In the second embodiment, the alteration light source unit 302 functions as an alteration unit.

The control unit 303 performs an overall control on the bio-optical measurement device 300 by transmitting instruction information or data corresponding to each unit of the bio-optical measurement device 300. The control unit 303 is implemented using a CPU and the like. The control unit 303 includes a calculator 291, a usage history determining unit 293, an output control unit 294, and a light source control unit 303a.

When an instruction signal that terminates a measurement of the object S1 to be measured is input from the input unit 26, the light source control unit 303a causes the light source unit 301 to stop radiating an illumination light as an alteration process, and causes the alteration light source unit 302 to radiate an alteration light to the measurement probe 3.

Figure 5:
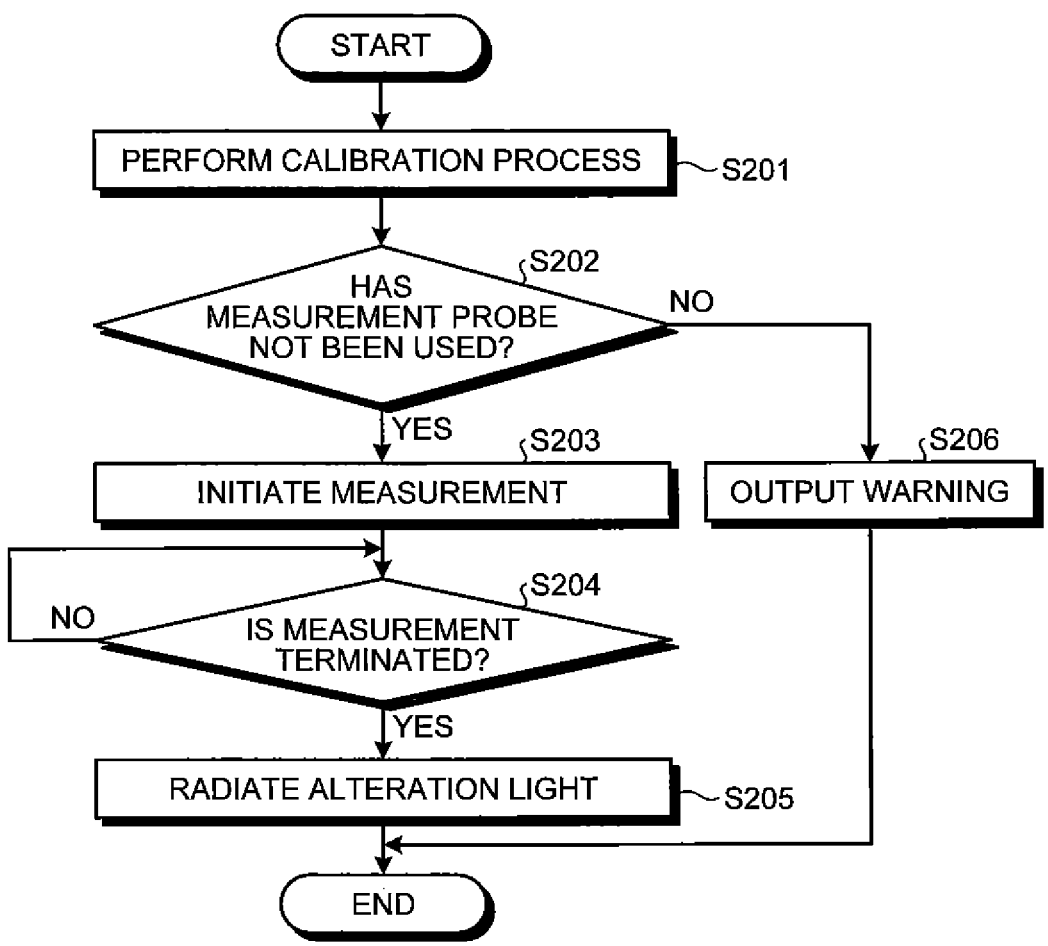
FIG. 5 is a flowchart illustrating processes performed by the bio-optical measurement system according to the second embodiment of the present invention.

A process performed by the bio-optical measurement system 10 configured as described above will be described. FIG. 5 is a flowchart illustrating an outline of a process performed by the bio-optical measurement system 10.

Steps S201 to S204 of FIG. 5 correspond to steps S101 to S104 of FIG. 3, respectively.

In step S205, the light source control unit 303a causes the light source unit 301 to stop radiating an illumination light, and causes the alteration light source unit 302 to radiate an alteration light to the measurement probe 3 as an alteration process. In this way, the property of the proximal end portion 33 of each of the illumination fiber 31 and the light receiving fibers 32 of the measurement probe 3 alters. After step S205, the bio-optical measurement system 10 terminates this process.

Step S206 corresponds to step S106 of FIG. 3. After step S206, the bio-optical measurement system 10 terminates this process.

According to the above-described second embodiment of the present invention, when an instruction signal that terminates a measurement of the object S1 to be measured is input from the input unit 26, the light source control unit 303a causes the light source unit 301 to stop radiating an illumination light as an alteration process, and causes the alteration light source unit 302 to radiate an alteration light to the measurement probe 3, thereby altering the proximal end portion 33 of each of the illumination fiber 31 and the light receiving fibers 32 of the measurement probe 3. In this way, without degrading accuracy of an examination result, it is possible to reliably prevent the disposable measurement probe 3 from being reused.

Third Embodiment

Next, a third embodiment of the present invention will be described. A bio-optical measurement system according to the third embodiment further includes a connector portion to which a distal end portion of a measurement probe may be inserted. For this reason, when description is made, the same element as that of the bio-optical measurement system according to the above-described second embodiment will be denoted by the same reference numeral.

Figure 6:
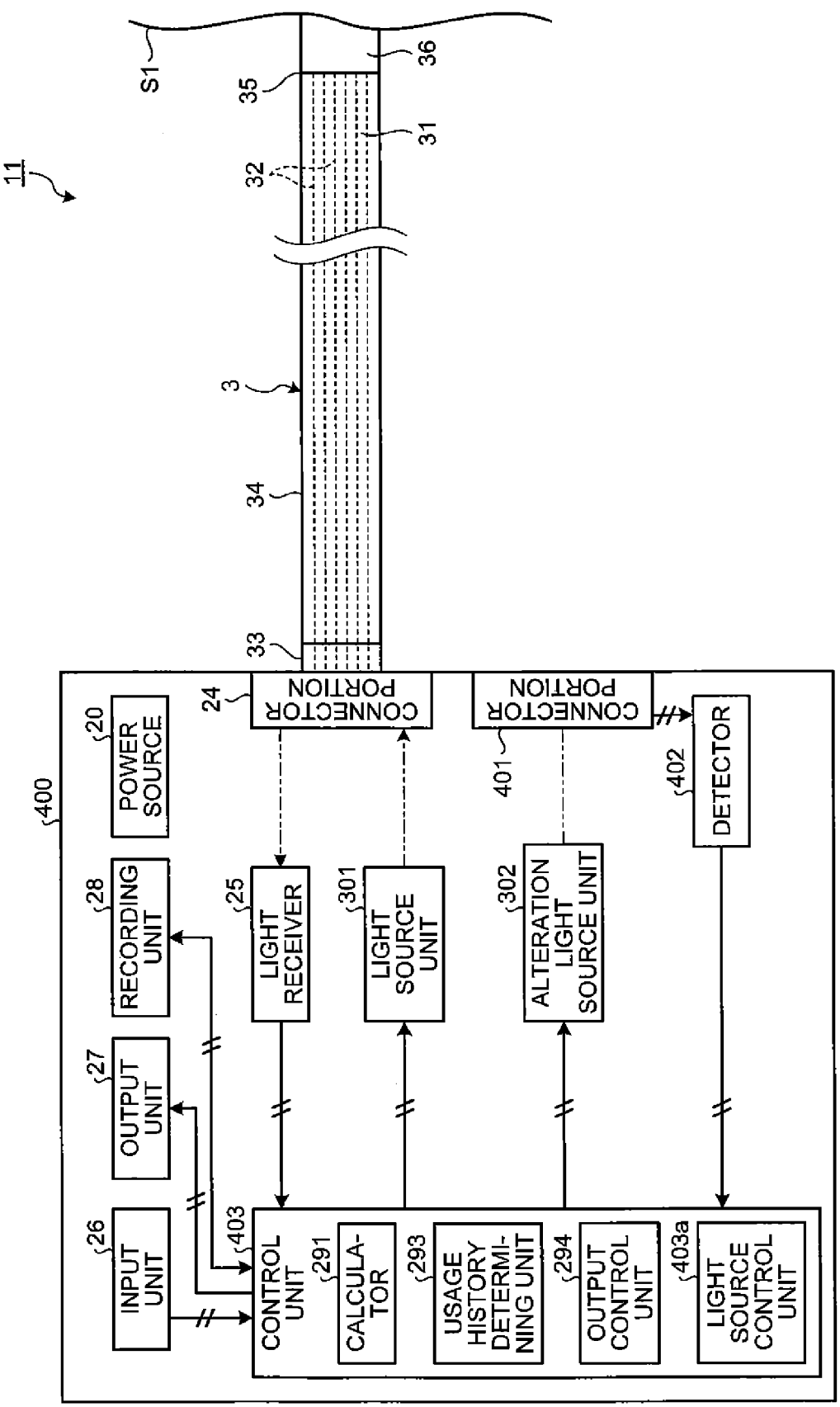
FIG. 6 is a block diagram schematically illustrating a configuration of a bio-optical measurement system according to a third embodiment of the present invention.

FIG. 6 is a block diagram schematically illustrating a configuration of a bio-optical measurement system according to the third embodiment of the present invention.

A bio-optical measurement system 11 illustrated in FIG. 6 includes a measurement probe 3 and a bio-optical measurement device 400 that detects the property of an object S1 to be measured by performing an optical measurement on the object S1 to be measured.

The bio-optical measurement device 400 includes a power source 20, a connector portion 24, a light receiver 25, an input unit 26, an output unit 27, a recording unit 28, a light source unit 301, an alteration light source unit 302, a connector portion 401, a detector 402, and a control unit 403.

A rod lens 36 of the measurement probe 3 may be inserted into the connector portion 401, and the connector portion 401 propagates an alteration light radiated from the alteration light source unit 302 to the rod lens 36 of the measurement probe 3.

The detector 402 detects whether the rod lens 36 of the measurement probe 3 is inserted into the connector portion 401. The detector 402 is implemented using a pressure sensor, a pull switch, and the like. When the rod lens 36 of the measurement probe 3 is inserted into the connector portion 401, and thus an insertion of the measurement probe 3 is detected, the detector 402 outputs a detection result to the control unit 403.

The control unit 403 performs an overall control on the bio-optical measurement device 400 by transmitting instruction information or data corresponding to each unit of the bio-optical measurement device 400. The control unit 403 is implemented using a CPU and the like. The control unit 403 includes a calculator 291, a usage history determining unit 293, an output control unit 294, and a light source control unit 403a.

When the detector 402 detects an insertion of the rod lens 36 of the measurement probe 3, the light source control unit 403a causes the light source unit 301 to stop radiating an illumination light as an alteration process, and causes the alteration light source unit 302 to radiate an alteration light to the connector portion 401.

Figure 7:
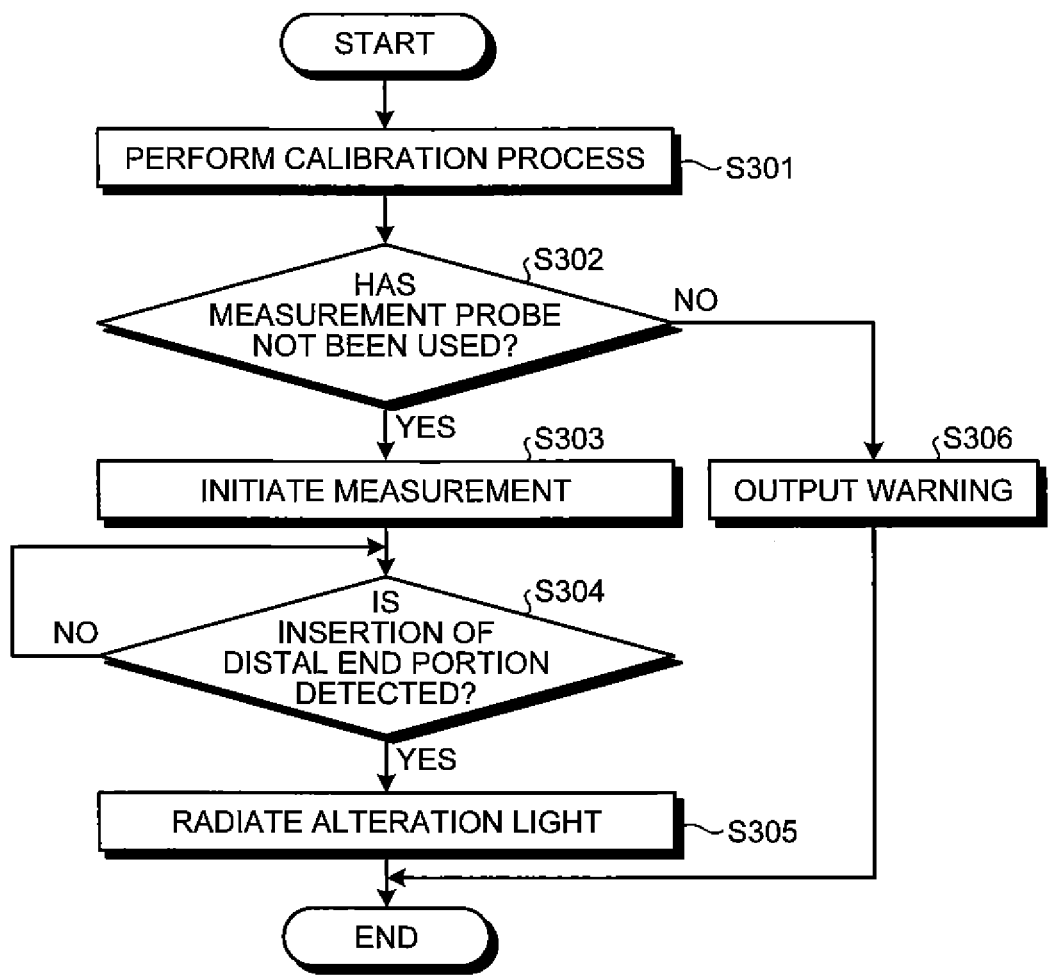
FIG. 7 is a flowchart illustrating processes performed by the bio-optical measurement system according to the third embodiment of the present invention.

A process performed by the bio-optical measurement system 11 configured as described above will be described. FIG. 7 is a flowchart illustrating an outline of a process performed by the bio-optical measurement system 11.

Steps S301 to S303 of FIG. 7 correspond to steps S101 to S103 of FIG. 3, respectively.

In step S304, when the detector 402 detects an insertion of the rod lens 36 of the measurement probe 3 into the connector portion 401 (Yes in step S304), the light source control unit 403a stops an illumination light radiated by the light source unit 301, and causes the alteration light source unit 302 to radiate an alteration light to the connector portion 401 as an alteration process (step S305). In this way, the property of the rod lens 36 of the measurement probe 3 is altered due to the alteration light. After step S305, the bio-optical measurement system 11 terminates this process.

In step S304, when the detector 402 fails to detect an insertion of the rod lens 36 of the measurement probe 3 into the connector portion 401 (No in step S304), the bio-optical measurement system 11 repeats the determination of step S304.

Step S306 corresponds to step S106 of FIG. 3. After step S106, the bio-optical measurement system 11 terminates this process.

According to the above-described third embodiment of the present invention, when the detector 402 detects an insertion of the rod lens 36 of the measurement probe 3, the light source control unit 403a stops an illumination light radiated by the light source unit 301, and causes the alteration light source unit 302 to radiate an alteration light to the connector portion 401, thereby altering an optical property of the rod lens 36. In this way, without degrading accuracy of an examination result, it is possible to reliably prevent the disposable measurement probe 3 from being reused.

Fourth Embodiment

Next, a fourth embodiment of the present invention will be described. A bio-optical measurement system according to the third embodiment further includes a mark generator that adds a mark indicating that a measurement probe has been used to a proximal end portion of the measurement probe. For this reason, hereinafter, when description is made, the same element as that of the bio-optical measurement system according to the above-described second embodiment will be denoted by the same reference numeral.

Figure 8:
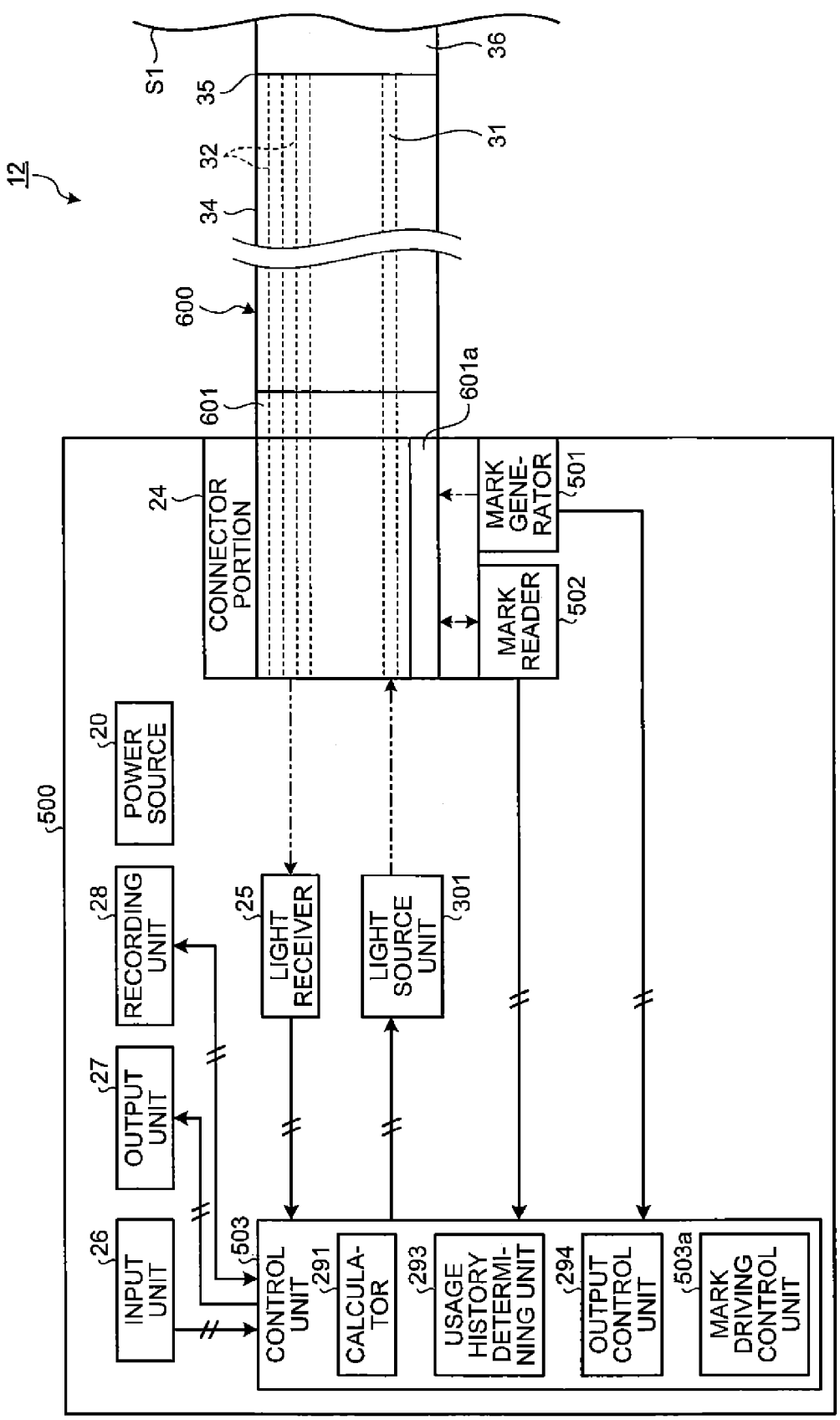
FIG. 8 is a block diagram schematically illustrating a configuration of a bio-optical measurement system according to a fourth embodiment of the present invention.

FIG. 8 is a block diagram schematically illustrating a configuration of a bio-optical measurement system according to the fourth embodiment of the present invention.

A bio-optical measurement system 12 illustrated in FIG. 8 includes a bio-optical measurement device 500 that detects the property of an object S1 to be measured, and a measurement probe 600 that may be attached to and detached from the bio-optical measurement device 500 and is used as a disposable medical device inserted into a subject.

First, the bio-optical measurement device 500 will be described. The bio-optical measurement device 500 includes a power source 20, a connector portion 24, a light receiver 25, an input unit 26, an output unit 27, a recording unit 28, a light source unit 301, a mark generator 501, a mark reader 502, and a control unit 503.

The mark generator 501 radiates light having a specified wavelength band to the measurement probe 600 to be described below. The mark generator 501 is implemented using, for example, an ultraviolet lamp that emits ultraviolet light. In the fourth embodiment, the mark generator 501 functions as an alteration unit.

The mark reader 502 reads a mark generated in the measurement probe 600 by the mark generator 501, and outputs read information to the control unit 503. The mark reader 502 is implemented using, for example, a light source that radiates visible light, and a light receiving element such as a photointerrupter that receives light radiated by the light source and reflected from the measurement probe 3.

The control unit 503 performs an overall control on the bio-optical measurement device 500 by transmitting instruction information or data corresponding to each unit of the bio-optical measurement device 500. The control unit 503 is implemented using a CPU and the like. The control unit 503 includes a calculator 291, a usage history determining unit 293, an output control unit 294, and a mark driving control unit 503a.

When an instruction signal that terminates a measurement of an object S1 to be measured is input from the input unit 26, the mark driving control unit 503a causes the measurement probe 600 to generate a mark indicating that it has been used by causing the mark generator 501 to radiate light.

Next, the measurement probe 600 will be described. The measurement probe 600 includes a plurality of light fibers. Specifically, the measurement probe 600 is implemented using an illumination fiber 31 that radiates an illumination light to the object S1 to be measured, and a plurality of light receiving fibers 32 where an optical feedback of an illumination light enters at different angles. The illumination fiber 31 and the light receiving fibers 32 are arranged such that distal end portions are parallel to each other. The measurement probe 600 includes a proximal end portion 601, a flexible portion 34, a distal end portion 35, and a rod lens 36.

The proximal end portion 601 is detachably connected to the connector portion 24. The proximal end portion 601 is provided with a mark generator 601a. The mark generator 601a receives and alters light radiated by the mark generator 501. The mark generator 601a generates a mark indicating the completion of use through the action of light. For example, the mark generator 601a is implemented using a photosensitive element such as a photochromic compound, and is colored by an ultraviolet ray radiated by the mark generator 501, thereby generating a mark indicating completion of use.

Figure 9:
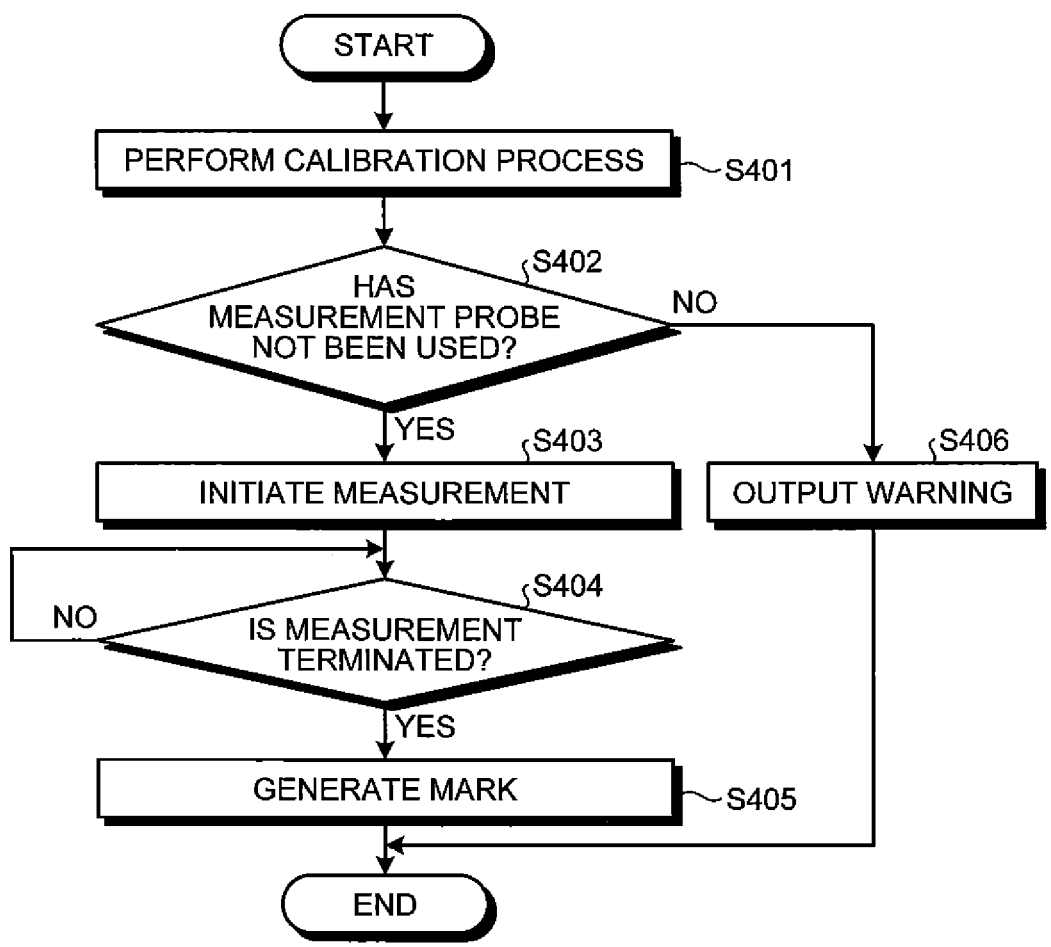
FIG. 9 is a flowchart illustrating processes performed by the bio-optical measurement system according to the fourth embodiment of the present invention.

A process performed by the bio-optical measurement system 12 configured as described above will be described. FIG. 9 is a flowchart illustrating an outline of a process performed by the bio-optical measurement system 12.

Step S401 of FIG. 9 corresponds to step S101 of FIG. 3. Subsequently, the usage history determining unit 293 determines whether the measurement probe 600 has not been used based on information read by the mark reader 502. Specifically, the usage history determining unit 293 determines whether a mark is generated in the mark generator 601a based on information read from the mark generator 601a by the mark reader 502. When the usage history determining unit 293 determines that the measurement probe 600 has not been used (Yes in step S402), the bio-optical measurement system 12 proceeds to step S403.

Step S403 and step S404 correspond to step S103 and step S104 of FIG. 3, respectively.

In step S405, the mark driving control unit 503a causes the mark generator 601a to generate a mark by causing the mark generator 501 to radiate light. In this way, a mark indicating completion of use of the measurement probe 600 is generated in the mark generator 601a of the measurement probe 600. After step S405, the bio-optical measurement system 12 terminates this process.

In step S402, when the usage history determining unit 293 determines that the measurement probe 600 has been used (No in step S402), the output control unit 294 gives warning by causing the output unit 27 to output an indication indicating the completion of use of the measurement probe 600 (step S406). Thereafter, the bio-optical measurement system 12 terminates this process.

According to the above-described fourth embodiment, when an instruction signal that terminates a measurement of the object S1 to be measured is input from the input unit 26, the mark driving control unit 503a causes the mark generator 501 to radiate light, thereby causing the mark generator 601a of the measurement probe 600 to generate a mark indicating completion of use of the measurement probe 600. In this way, without degrading accuracy of an examination result, it is possible to reliably prevent the disposable measurement probe 600 from being reused.

In the fourth embodiment, the mark generator 601a reacts to an ultraviolet ray. However, a photosensitive element or a photosensitive pigment that reacts to light having a wavelength band of red and blue may be applied.

In addition, in the fourth embodiment, the mark generator 601a is exposed to an ultraviolet ray, thereby causing the mark generator 601a to generate a mark. However, for example, a mark may be generated by heat. In this case, the mark generator is formed using a member that may be deformed by heat, and the mark generator 501 may deform the mark generator 601a by heat, thereby generating a mark indicating completion of use of the measurement probe 600.

In addition, in the fourth embodiment, instead of a mark indicating completion of use, the mark generator 501 applies a voltage to the mark generator 601a to change a conductivity of the mark generator 601a. In this way, it is possible to cause the mark generator 601a to function as a mark indicating completion of use of the measurement probe 600.

In addition, in the fourth embodiment, description has been made using the measurement probe 600 as a disposable medical device. However, for example, a disposable medical device such as an electrosurgical knife, a catheter, and a treatment tool used for laparoscopic surgery may be applied.
Other Embodiments In the present invention, a measurement probe or a mark generator may be formed using a member, the property of which alters by an infrared ray (for example, 0.7 μm to 1 mm), and an infrared ray may be radiated to the measurement probe, thereby altering the property of the measurement probe.

According to some embodiments, since a control unit causes an alteration unit to alter a disposable medical device at the end of a treatment using a medical apparatus, it is possible to reliably prevent the disposable medical device from being reused without degrading accuracy of an examination result.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical apparatus that performs a specified treatment and is detachably connectable with a disposable measurement probe including a plurality of light fibers each made of a material which alters due to a transmission of light in a specified wavelength band, the medical apparatus comprising:
   an alteration unit that performs an alteration process of altering the measurement probe and that includes:
      a light source unit that radiates an illumination light to the measurement probe, the illumination light including light in the specified wavelength band as a component;
      a filter that transmits light included in the illumination light radiated by the light source unit other than light in the specified wavelength band; and
      a filter driving unit that moves the filter between a first position passing through a light path of the illumination light radiated by the light source unit and a second position away from a position of the light path;
   a control unit that causes the alteration unit to perform the alteration process at the end of the treatment by the medical apparatus; and
   an input unit that receives an input of an instruction signal that terminates the treatment by the medical apparatus, wherein when the instruction signal is input from the input unit, the control unit drives the filter driving unit as the alteration process to move the filter from the first position to the second position.

2. The medical apparatus according to claim 1, wherein the light in the specified wavelength band is an ultraviolet ray.

3. A medical apparatus that performs a specified treatment and is detachably connectable with a disposable measurement probe including a plurality of light fibers each made of a material which alters due to a transmission of light in a specified wavelength band, the medical apparatus comprising:
   an alteration unit that performs an alteration process of altering the measurement probe and that includes:
      a light source unit that radiates an illumination light to the measurement probe, the illumination light including light in the specified wavelength band as a component, and
      an alteration light source unit that radiates the light in the specified wavelength band to the measurement probe;
   a control unit that causes the alteration unit to perform the alteration process at the end of the treatment by the medical apparatus; and
   an input unit that receives an input of an instruction signal that terminates the treatment by the medical apparatus, wherein when the instruction signal is input from the input unit, the control unit stops the illumination light radiated by the light source unit as the alteration process, and causes the alteration light source unit to radiate the light in the specified wavelength band.

4. A medical apparatus that performs a specified treatment and is detachably connectable with a disposable measurement probe including a plurality of light fibers each made of a material which alters due to a transmission of light in a specified wavelength band, the medical apparatus comprising:
   a connector portion where a distal end portion of the measurement probe is to be inserted;
   a detector that detects whether the distal end portion is inserted into the connector portion;
   an alteration unit that performs an alteration process of altering the measurement probe and that includes:

a light source unit that radiates an illumination light to the measurement probe, the illumination light including light in the specified wavelength band as a component, and an alteration light source unit that radiates the light in the specified wavelength band to the connector portion; and a control unit that causes the alteration unit to perform the alteration process at the end of the treatment by the medical apparatus, wherein when the detector detects insertion of the distal end portion, the control unit stops the illumination light radiated by the light source unit as the alteration process, and causes the alteration light source unit to radiate the light in the specified wavelength band as the alteration process.

5. A medical apparatus that performs a specified treatment and is detachably connectable with a disposable measurement probe including a plurality of light fibers each made of a material which alters due to a transmission of light in a specified wavelength band, the medical apparatus comprising:

an alteration unit that radiates, as an alteration process, an illumination light to the measurement probe, the illumination light including light in the specified wavelength band as a component;

a control unit causes the alteration unit to perform the alteration process at the end of the treatment by the medical apparatus;

a light receiver that receives an optical feedback of the illumination light which is radiated through the measurement probe and is reflected and/or scattered from a white plate attached to a distal end portion of the measurement probe; and an output unit that outputs information indicating completion of use of the measurement probe, wherein, when a value of the optical feedback received by the light receiver is not greater than or equal to a specified threshold value, the control unit causes the output unit to output the information.

6. A medical system comprising:

a medical apparatus that performs a specified treatment; and a disposable measurement probe to be detachably connected to the medical apparatus and to be inserted into a subject, the measurement probe including a plurality of light fibers each made of a material which alters due to a transmission of light in a specified wavelength band, wherein the medical apparatus includes:

an alteration unit that performs an alteration process of altering the measurement probe and that includes:

a light source unit that radiates an illumination light to the measurement probe, the illumination light including light in the specified wavelength band as a component, a filter that transmits light included in the illumination light radiated by the light source unit other than light in the specified wavelength band, and a filter driving unit that moves the filter between a first position passing through a light path of the illumination light radiated by the light source unit and a second position away from a position of the light path, a control unit that causes the alteration unit to perform the alteration process at the end of the treatment by the medical apparatus, and an input unit that receives an input of an instruction signal that terminates the treatment by the medical apparatus, wherein when the instruction signal is input from the input unit, the control unit drives the filter driving unit as the alteration process to move the filter from the first position to the second position.

* * * * *